United States Patent [19]

Boast

[11] Patent Number: 4,705,781
[45] Date of Patent: Nov. 10, 1987

[54] METHOD OF TREATING CEREBRAL ISCHEMIA USING 4-(PHOSPHONO SUBSTITUTED LOWER ALKYL OR LOWER ALKENYL)PIPERAZINE-2-CARBOXYLIC ACIDS AND SALTS, ESTERS AND AMIDES THEREOF

[75] Inventor: Carl A. Boast, Maplewood, N.J.

[73] Assignee: Giba-Geigy Corporation, Ardsley, N.Y.

[21] Appl. No.: 916,967

[22] Filed: Oct. 8, 1986

[51] Int. Cl.$^4$ ............................................ A61K 31/675
[52] U.S. Cl. ....................................................... 514/85
[58] Field of Search .......................................... 514/85

[56] References Cited

FOREIGN PATENT DOCUMENTS 159889 10/1985 European Pat. Off. .
2157685 10/1985 United Kingdom ................ 544/337

OTHER PUBLICATIONS

DeBannol et al, Chem. Abst. 99—(1983).
De Montigney et al, Chem. Abst. 101—(1984) 52502p.

Watkins et al, Chem. Abst. 207305 Q(1986).

Primary Examiner—Stanley J. Friedman
Attorney, Agent, or Firm—Michael W. Glynn; Irving M. Fishman

[57] ABSTRACT

A method of treating or preventing ischemic brain damage in a mammal comprising administering to said mammal in need of the same an effective anti-ischemic amount of a compound of the formula

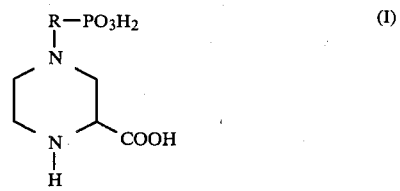

where R is lower alkylene or lower alkenylene; and the pharmaceutically acceptable salts, esters and amides thereof.

7 Claims, No Drawings

METHOD OF TREATING CEREBRAL ISCHEMIA USING 4-(PHOSPHONO SUBSTITUTED LOWER ALKYL OR LOWER ALKENYL)PIPERAZINE-2-CARBOXYLIC ACIDS AND SALTS, ESTERS AND AMIDES THEREOF

The present invention relates to a method of treating or preventing ischemic brain damage in a mammal comprising the administration to the mammal of an effective anti-ischemic amount of a compound of the formula

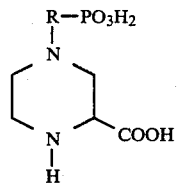

wherein R is lower alkylene or lower alkenylene, and the pharmaceutically acceptable salts thereof, and wherein the carboxy group and/or the phosphono group may be in the form of the corresponding pharmaceutically acceptable carboxylate ester or amide and pharmaceutically acceptable phosphono ester or amide, respectively.

In a preferred embodiment, the compound of formula I is in the form of the free acid or the pharmaceutically acceptable salts thereof. In a subembodiment thereof, R is preferably alkylene of 3 to 4 carbon atoms and has a chain length of three carbon atoms between the piperazine nitrogen and the phosphono moiety. In an alternate subembodiment, R is alkylene of 1 to 2 carbon atoms and has a chain length of one carbon atom between the piperazine nitrogen and the phosphono moiety. Most preferably R is 1,3-propylene or methylene.

The compounds according to formula I can be used in their racemic form or in the form of the optical antipode thereof.

In an alternate preferred embodiment, R is alkenylene of 3 to 5 carbon atoms and has a chain length of at least 3 carbon atoms, more preferably R is alkenylene of 3 to 4 carbon atoms, and has a chain length of 3 carbon atoms, and most preferably R is 1,3-prop-1-enylene, i.e. where the double bond is adjacent to the phosphono moiety.

The term "lower", when referred to above and hereinafter in connection with organic groups, radicals or compounds respectively, defines such with up to and including 7, preferably up to and including 4 and advantageously one, two or three carbon atoms.

A pharmaceutically acceptable carboxylate ester within the context of the present invention represents an ester of a compound of the invention having a carboxy group, preferably a carboxlic acid prodrug ester that may be convertible under physiological conditions to the corresponding free carboxlic acid.

Carboxy esterified in form of a pharmaceutically acceptable ester, preferably represents e.g. lower alkoxycarbonyl; (amino, mono- or di-lower alkylamino) -substituted straight chain $C_2$–$C_5$ lower alkoxycarbonyl; carboxy substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. unsubstituted or substituted benzyloxycarbonyl or pyridylmethoxycarbonyl; lower alkanoyloxy-substituted methoxycarbonyl, e.g. pivaloyloxymethoxycarbonyl; (lower alkanoyloxy or lower alkoxy) -substituted lower alkoxymethoxy carbonyl; bicyclo[2,2,1]heptyloxycarbonyl-substituted methoxycarbonyl such as bornyloxycarbonylmethoxycarbonyl; 3-phthalidoxycarbonyl; (lower alkyl, lower alkoxy, halo) -substituted 3-phthalidoxycarbonyl; lower alkoxycarbonyloxy lower alkoxycarbonyl, e.g. 1-(methoxy- or ethoxycarbonyloxy)-ethoxycarbonyl.

Most preferred prodrug esters are e.g. the $C_1$–$C_4$-alkyl esters such as ethyl or isobutyl; the lower alkanoyloxymethyl esters such as pivaloyloxymethyl; the dilower alkylamino-straight chain $C_2$–$C_4$-alkyl esters such as 2-diethyl-aminoethyl; the pyridylmethyl esters such as 3-pyridylmethyl.

A pharmaceutically acceptable amide within the context of the present invention represents an amide of a compound of the invention having a carboxy group, preferably a carboxylic acid amide that may be convertible under physiological conditions to the corresponding free carboxylic acid.

Preferred amides are compounds of the invention wherein carboxy is derivatized as carbamoyl, N-monolower alkylcarbamoyl such as N-ethylcarbamoyl, N,N-di-lower alkylcarbamoyl such as N,N-diethylcarbamoyl, or di-lower aklylamino-N-lower alkylcarbamoyl such as N-(2-diethylaminoethyl) carbamoyl or N-(3-diethylaminopropyl)carbamoyl.

Pharmaceutically acceptable salts are preferably metal or ammonium salts or said compounds of the invention having a free phosphonic or carboxy group, more particularly alkali or alkaline earth metal salts, e.g. the sodium, potassium, magnesium or calcium salt; or advantageously crystallizing ammonium salts derived from ammonia or organic amines, such as methylamine, diethylamine, triethylamine, dicylohexylamine, triethanolamine, ethylenediamine, tris-(hydroxymethyl)aminomethane or benzyltrimethylammonium hydroxide. The compounds of the invention which are basic amines form acid addition salts of preferably pharmaceutically acceptable inorganic or organic acids, such as of strong mineral acids, for example hydrohalic, e.g. hydrochloric or hydrobromic acid; sulfuric, phosphoric or nitric acid; allphatic or aromatic carboxylic or sulfonic acids, e.g. acetic, propionic, succinic, glycolic, lactic, malic, tartaric, gluconic, citric, ascorbic, maleic, fumaric, pyruvic, pamoic, nicotinic, methanesulfonic, ethanesulfonic, hydroxyethanesulfonic, benzenesulfonic, p-toluenesulfonic or naphthalenesulfonic acid.

A pharmaceutically acceptable phosphono ester within the context of the present invention represents an ester of a compound having a phosphono group, preferably a phosphonic acid prodrug ester that may be convertible under physiological conditions to the free phosphonic acid.

Phosphono esterified in form of a pharmaceutically acceptable ester preferably represents e.g. mono- or di-lower alkoxy phosphono wherein the lower alkoxy groups are independently unsubstituted or are substituted by: amino; mono- or di-lower alkylamino; carboxy; lower alkoxycarbonyl; or aryl, such as phenyl, halophenyl, lower alkoxyphenyl or pyridyl; or is mono- or di-methoxy phosphono wherein the methoxy groups are substituted by: lower alkanoyloxy; or mono- or bi-cycloalkoxycarbonyl; or the like.

Most preferred prodrug phosphono esters are e.g. the straight chain lower alkyl esters, such as the monoethyl ester; the lower alkanoyloxymethyl esters such as the monopivaloyloxymethyl; and the mono-pyridylmethyl esters such as the mono-3-pyridylmethyl ester.

A pharmaceutically acceptable phosphonoamide within the context of the present invention represents a phosphono mono- or di-amide, preferably an amide that may be convertible under physiological conditions to the corresponding free phosphonic acid.

Preferred phosphonoamides are the mono- and di-amide, the mono- and di-(mono- or di-lower alkyl)amides, such as the mono-N-ethylamide, the di-N-ethylamide or the mono-N-diethyl amide.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents such as ethanol.

The compounds of the present invention are known and described in commonly assigned copending U.S. patent application Ser. No. 849,664 filed Apr. 9, 1986, relating to the aforementioned compounds, their preparation, their use as anxiolytic agents, and anxiolytically effective compositions thereof, the disclosure of which is incorporated herein by reference in toto.

Moreover, certain of the compounds useful in accordance with the instant invention are disclosed in European Patent Application No. 0159889, published Oct. 30, 1985. For example, the European Patent Application discloses 3-(($\pm$)-2-carboxypiperazin-4-yl)-propyl-1-phosphonic acid as an anticonvulsant.

Surprisingly and unexpectedly, however, the compounds of formula I have now been found to be useful in preventing and treating cerebral ischemia, an indication neither disclosed nor suggested in the aforementioned disclosures.

Presently, there are no U.S. Food and Drug Administration approved drugs available for preventing or limiting brain damage with gives rise to the persistant effects resulting from stroke. Stroke is presently the third leading cause of death in the U.S. Approximately 400,000 people suffer from strokes in the U.S. every year. Of these, some 40% are left at least partially paralyzed, unable to talk or otherwise debilitated. The instant class of compounds of formula I offer a novel but practical approach in ameliorating, or limiting, the effect of cerebral ischemia in mammals, including man.

Certain amino acids are involved in communication between brain cells, or neurons, and are consequently designated as neurotransmitters. Some of these amino acid transmitters are inhibitory, in that they slow down neuronal activity, while others are excitatory in that they increase neuronal activity. Under conditions of cerebral ischemia, occasioned by, inter alia, stroke, excessive quantities of these amino acids may be released, spilling onto neighboring neurons. In brain areas where there are large amounts of excitatory amino acid transmitters, the result is a massive abnormal increase in neuronal activity. This excessive activation characteristically results in the buildup of toxic materials in the brain cells, ultimately causing cell death. The neurons, in other words, are literally excited to death. When a sufficient number of neurons die, serious impairment, such as reduced limb movement or sensation, or speech or memory impairment, characteristically follows. While not to be limited to the actual mode of action, it is believed that the instant compounds of formula I act to inhibit receptors responsive to such excitatory amino acids, thereby damping the aforementioned abnormal increase in neuronal activity.

The use of the compounds of formula I in the treatment or prevention of ischemic brain damage is demonstrable in in vivo animal tests using mammal test models, e.g. mice, rats, gerbils or monkeys.

Said compounds can be administered enterally or parenterally, advantageously orally or transdermally, or subcutaneously, intravenously or intraperitoneally, for example, within gelatin capsules or tablets if taken orally, or in the form of aqueous suspensions or solutions, and the like. The applied in vivo dosage may range between about 0.01 and about 100 mg/kg, preferably between about 0.05 and about 50 mg/kg, advantageously between about 0.1 and 10 mg/kg body weight of the host recipient. The optimum dosage of the active compound according to formula I administered is, of course, dependent on the species of warm-blooded animal, or mammal, the body weight, age and individual condition of the mammalian host, and on the form of administration.

Preferably, the compounds of formula I are administered in the form of a pharmaceutical composition suitable for the desired form of administration.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of formula I with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In a preferred embodiment of the present invention cerebral ischemia is treated or prevented in a mammal in need of the same, by parenteral administration, e.g. subcutaneously, intravenously or intraperitoneally.

The following example is intended to illustrate the invention and is not to be construed as being a limitation thereon.

EXAMPLE

2 Mg/ml 3-((±)-2-carboxypiperazin-4-yl)propyl-1-phosphonic acid (CPP) was dissolved in an aqueous saline solution and injected intraperitoneally in an amount of 10 mg CPP per kg body weight into female gerbils weighing between 50–70 g. Fifteen minutes later, under Metofane anesthesia, the carotid arteries were exposed and blood flow to the brain was prevented for twenty minutes by using aneurysm clips. CPP (2 mg/ml saline) in an amount of 10 mg/kg was injected again into said gerbils 2, 4 and 6 hours later. As a control, a second group of gerbils were injected with saline instead of CPP and also had carotid blood flow prevented for 20 minutes by using aneurysm clips. Behavioral measures of motor activity were recorded 1 and 4 days after the drug/surgical treatment. Following decapi-tation, brains were removed and thin sections were stained for evaluation of brain damage. The saline treated control gerbils showed increased motor activity and extensive but selective (CA1 of hippocampus) brain damage, whereas the CPP pretreated gerbils exhibited a significantly reduced degree of brain damage as shown in the following TABLE 1:

TABLE 1

| | Motor Activity | | | | |
|---|---|---|---|---|---|
| | 24 h 15 min | 24 h 30 min | 4 day 15 min | 4 day 30 min | BDR* |
| Ischemia (control) | | | | | |
| Mean | 3035 | 2096 | 2314 | 1281 | 3 |
| SEM | 265 | 252 | 237 | 188 | |
| CPP treated | | | | | |
| Mean | 3360 | 2082 | 1816 | 1020 | 1** |
| SEM | 325 | 307 | 190 | 160 | |

*BDR = Brain Damage Rating
**p < .05 vs. Ischemia, Mann - Whitney test

The motor activity data represent the mean or standard error of the mean (SEM) of the distance traveled in inches during a 15 min period. Means are based on 35 animals in the Ischemia group, and 27 animals in the CPP group. In this experiment CPP (10 mg/kg, i.p.) was injected 15 min prior to carotid occlusion and again 2, 4 and 6 hours later.

In a second study, the identical protocol was followed except that the first injection of CPP, and pure saline in the control group, was delayed until after the 20 minute carotid occlusion. Again the saline post treated control gerbils exhibited increased motor activity and extensive brain damage as compared to the CPP post treated gerbils, as shown in the following TABLE 2:

TABLE 2

| | Motor Activity | | | | |
|---|---|---|---|---|---|
| | 24 h 15 min | 24 h 30 min | 4 day 15 min | 4 day 30 min | BDR* |
| Ischemia (control) | | | | | |
| Mean | 2893 | 2026 | 2049 | 1090 | 3 |
| SEM | 270 | 326 | 297 | 201 | |
| CPP treated | | | | | |
| Mean | 3548 | 2792 | 1153** | 573** | 1** |
| SEM | 607 | 640 | 133 | 130 | |

*BDR = Brain Damage Rating
**p < .05 vs. Ischemia, Mann - Whitney test for BDR, t-test for motor activity.

The motor activity data represent the mean or standard error of the mean (SEM) of the distance traveled in inches during a 15 min period. Means are based on 17 animals in the Ischemia group, and 12 animals in the CPP group. In this experiment CPP (10 mg/kg, i.p.) was injected immediately after carotid occlusion and again 2, 4 and 6 hours later.

What is claimed is:

1. A method of treating or preventing ischemic brain damage in a mammal, comprising administering to said mammal in need of the same an effective anti-ischemic amount of a compound of the formula $$\begin{array}{c} R-PO_3H_2 \\ | \\ N \\ \diagup \quad \diagdown \\ \diagdown \quad \diagup \\ N \quad COOH \\ | \\ H \end{array}$$

wherein R is lower alkylene or lower alkenylene; and the pharmaceutically acceptable salts, esters and amides thereof.

2. A method according claim 1, wherein said ischemic brain damage is occasioned by stroke.

3. A method according to claim 1, wherein the compound of formula I is in the form of the free acid or a pharmaceutically acceptable salt thereof.

4. A method according to claim 3, wherein R is 1,3-propylene or is methylene.

5. A method according to claim 2, wherein the compound of formula I is in the form of the free acid or a pharmaceutically acceptable salt thereof and R is 1,3-propylene or methylene.

6. A method according to claim 4, wherein R is methylene.

7. A method according to claim 5, wherein R is methylene.

* * * * *